(12) United States Patent
Farra (10) Patent No.: US 8,679,093 B2
(45) Date of Patent: Mar. 25, 2014

(54) MULTI-DOSE DRUG DELIVERY DEVICE AND METHOD

(75) Inventor: Robert Farra, Acton, MA (US)

(73) Assignee: MicroCHIPS, Inc., Lexington, MA (US)

( * ) Notice: Subject to any disclaimer, the term of this patent is extended or adjusted under 35 U.S.C. 154(b) by 37 days.

(21) Appl. No.: 13/302,863

(22) Filed: Nov. 22, 2011

(65) Prior Publication Data

US 2012/0130339 A1    May 24, 2012

Related U.S. Application Data

(60) Provisional application No. 61/416,455, filed on Nov. 23, 2010.

(51) Int. Cl.
*A61K 9/22* (2006.01)

(52) U.S. Cl.
USPC ........................................ 604/890.1

(58) Field of Classification Search
USPC ................................ 604/890.1, 891.1, 892.1
See application file for complete search history.

(56) References Cited

U.S. PATENT DOCUMENTS

| | | | |
|---|---|---|---|
| 4,450,150 A | 5/1984 | Sidman | |
| 5,017,381 A | 5/1991 | Maruyama et al. | |
| 5,023,088 A | 6/1991 | Wong et al. | |
| 5,209,746 A | 5/1993 | Balaban et al. | |
| 5,429,822 A | 7/1995 | Gresser et al. | |
| 5,797,898 A | 8/1998 | Santini, Jr. et al. | |
| 6,491,666 B1 | 12/2002 | Santini, Jr. et al. | |
| 6,527,762 B1 | 3/2003 | Santini, Jr. et al. | |
| 6,976,982 B2 | 12/2005 | Santini, Jr. et al. | |
| 7,104,945 B2 | 9/2006 | Miller | |
| 7,214,206 B2 | 5/2007 | Rue et al. | |
| 2007/0275035 A1* | 11/2007 | Herman et al. | 424/426 |
| 2008/0081064 A1 | 4/2008 | Jelle et al. | |
| 2009/0196903 A1 | 8/2009 | Kliman et al. | |
| 2010/0119694 A1 | 5/2010 | Guo et al. | |
| 2010/0152704 A1 | 6/2010 | Lee et al. | |
| 2011/0060309 A1 | 3/2011 | Lee et al. | |
| 2011/0098640 A1 | 4/2011 | Horne et al. | |
| 2011/0152839 A1 | 6/2011 | Cima et al. | |
| 2011/0182967 A1 | 7/2011 | Canham et al. | |

FOREIGN PATENT DOCUMENTS

| WO | 8600519 A1 | 1/1986 |
|---|---|---|
| WO | 2011097634 A1 | 8/2011 |

* cited by examiner

*Primary Examiner* — Nicholas Lucchesi
*Assistant Examiner* — Pritesh Patel
(74) *Attorney, Agent, or Firm* — Sutherland Asbill & Brennan LLP (57) ABSTRACT

Drug delivery devices and methods are provided. The device included two or more housing units connected together end-to-end in a fixed, linear orientation, the exterior surfaces of the connected housing units defining a sidewall of the device; discrete drug dose units disposed within the housing units; degradable timing members connected to the housing units and separating the discrete dose units from one another; first and second end pieces defining opposed ends of the device such that the discrete dose units are located between the first and second end pieces within each of the housing units, wherein the device is configured to release in vivo a first of the discrete dose units following rupture of the first or second end piece, and subsequently to release in vivo a second of the discrete dose units following rupture of the degradable timing member separating the first discrete dose unit from the second discrete dose unit.

17 Claims, 9 Drawing Sheets

MULTI-DOSE DRUG DELIVERY DEVICE AND METHOD

CROSS-REFERENCE TO RELATED APPLICATIONS

The present application claims benefit to U.S. Provisional Application No. 61/416,455, filed Nov. 23, 2010. This application is incorporated herein by reference.

BACKGROUND

This disclosure is generally in the field of implantable medical devices. In particular, the disclosure relates to implantable devices for drug release over an extended period.

Implantable devices for the delivery of drugs to patients over extended periods are known. U.S. Pat. No. 5,797,898, U.S. Pat. No. 6,527,762, and U.S. Pat. No. 6,491,666, and U.S. Pat. No. 6,976,982 describe devices for the storage and controlled release of drug formulations from multi-reservoir devices. One category of the devices provide passive controlled release of multiple, individual doses of drug. The reservoirs contain a release system which comprises a drug. That is, the release system of each reservoir can be individually "programmed," e.g., formulated, to provide selected kinetics of drug release, controlling both the time at which release is initiated and the rate at which the drug is released. Release from different reservoirs can be staggered to provide complex release profiles. Reservoir caps may be provided to close off reservoir openings until such time as release of the drug is desired. Reservoir caps are designed to passively disintegrate or become permeable in vivo to initiate drug release.

It would be desirable to provide improved designs of such implantable devices for therapeutic or prophylactic treatments. It would in particular be desirable to provide small devices for precise, local (e.g., pinpoint) delivery of a drug over an extended period precisely to selected tissue sites, wherein the device has a relatively high drug volume to device volume ratio and can be implanted into a patient by a minimally invasive technique. It would be further desirable to provide devices having a relatively simple design that can be readily fabricated and assembled from relatively few components.

SUMMARY

Embodiments of the present devices and methods address at least some of the foregoing needs. In one aspect, a drug delivery device is provided that includes at least two housing units connected together end-to-end in a fixed, linear orientation, each housing unit having an exterior surface and an interior surface, and the exterior surfaces of the connected housing units defining a sidewall of the device. At least two discrete dose units, each comprising a drug formulation comprising at least one drug, are disposed within each of the housing units. At least one degradable timing member is connected to the at least two housing units and separates the discrete dose units from one another. A first end piece defines a first end of the device while a second end piece defines a second end of the device distal to the first end of the device. The discrete dose units are located between the first and second end pieces within each of the housing units. The device, when deployed in vivo, is adapted to release a first of the discrete dose units following rupture of the first or second end piece, and subsequently to release a second of the discrete dose units following rupture of the degradable timing member separating the first and second discrete dose units.

In another aspect, methods are provided for administering a drug to a patient. In one embodiment, the method includes injecting or otherwise inserting one or more of the above-described drug delivery devices into a tissue site in a patient and thereafter releasing the at least one discrete dose unit from the device to the tissue site.

In still another aspect, an implantable drug delivery device is provided that includes at least two solid units of a drug formulation which comprises at least one drug. The solid units each have a proximal end, a distal end, and one or more longitudinal exterior surfaces therebetween. At least one seal member is sandwiched between the proximal end of a first of the solid units and the distal end of a second of the solid units. A coating layer covers at least the longitudinal exterior surfaces of the solid units and is substantially non-permeable, such that release of the drug from the first or second solid unit is controlled at least in part, and preferably primarily or exclusively, by the in vivo disintegration of the seal member.

DETAILED DESCRIPTION

Implantable drug delivery devices have been developed that provide for the passively controlled release of drug, wherein the device has a high ratio of drug formulation volume to total device volume and the device can be deployed into a patient using minimally invasive conventional techniques and instruments.

In exemplary embodiments, the drug delivery device is shaped to allow insertion through a conventional needle (e.g., large gauge hypodermic needle or with a trocar) into a specific location in the body of a patient, such as a human or other mammal in need of treatment or prophylaxis. The targeted tissue location may be, for example, a lumen other than the vasculature, subcutaneous space, intramuscular, in a specific organ/tumor mass, peritoneal cavity, duodenum, intracranial cavity or brain tissue, or pleural space. The entire implantable drug delivery device is completely implanted into the targeted tissue or tissues, as distinct from a catheter, at least a portion of which generally protrudes/extends from the patient's body. Alternatively, the drug delivery device may be sized and shaped for oral administration. Embodiments of the drug delivery devices described herein advantageously are designed to provide a hermetic drug delivery device that is suitable for being packaged (e.g., in a sterile metal foil) and stored for a prolonged period of time (e.g., months to years) prior to being opened and implanted into the body of a patient.

Device Body and Structure

Generally described, an embodiment of an implantable drug delivery device comprises at least two housing units connected together end-to-end in a fixed, linear orientation. In exemplary embodiments, the devices have two or more discrete dose units of drug formulation disposed therein. Each housing unit has an exterior surface and an interior surface, the exterior surfaces of the connected housing units defining a sidewall of the device. The housing units are located between a first end piece defining a first end of the device and a second end piece defining a second end of the device distal to the first end of the device. At least two discrete dose units are disposed within the housing units located between the first and second end pieces. The device may further include degradable timing members connected to the housing units, e.g., connecting adjacent housing units, and separating the discrete dose units from one another. In embodiments, the first and second end pieces comprise degradable timing members. The timing members, the first end piece/degradable timing member/second end piece, and the interior surface of the housing unit to which the first end piece/degradable timing member/second end piece is connected together define a reservoir in which one of the dose units is disposed.

Desirably, the device is configured to control the release of each discrete dose unit when the device is deployed in vivo. For example, in an embodiment the device may be adapted to release a first discrete dose unit following rupture of the first or second end piece, and subsequently to release a second discrete dose unit following rupture of a degradable timing member. The device may release one or more additional discrete dose units following rupture of one or more additional degradable timing members. The dose unit may be a drug provided with or without excipients and with or without a matrix material.

In a preferred embodiment, the drug contains very little or no excipient in order to maximize the amount of drug per volume of the dose unit. For example, the dose unit may contain between 85 and 99 percent drug, e.g., 90 to 95 percent drug, with the remainder being one or more excipients useful for forming solid units, such as tablets.

In another exemplary embodiment, an implantable drug delivery device comprises at least two solid units of a drug formulation which comprises at least one drug. The solid units each have a proximal end, a distal end, and one or more longitudinal exterior surfaces therebetween. At least one seal member is sandwiched between the proximal end of a first solid unit and the distal end of a second solid unit. A coating layer that is substantially non-permeable covers at least the longitudinal exterior surfaces of the solid units. Desirably, the device is adapted to control the release of the drug from the solid units at least in part by the in vivo disintegration of the seal member. In particular embodiments, the coating layer is adapted to disintegrate in vivo after the in vivo disintegration of the seal member and release of the drug from the plurality of solid units.

The devices provided herein may be any shape and size suitable for delivery in a minimally invasive manner. In particular embodiments the device is elongated in shape, a non-limiting example of which includes a substantially tubular (or cylindrical) shape. As used herein, the term "elongated" is used broadly to include without limitation a shape wherein the longitudinal axis is longer than a lateral axis of the device.

It should be understood that there are many elongated implantable device geometries that could embody the concept of employing the discrete dose units described herein, and is not limited to a substantially tubular design. In a preferred embodiment, the device is in the form of a straight, rigid, elongated tube.

Any suitable number of reservoirs (including the housing units, dose units, and degradable timing members/seal members) may be disposed in the devices provided herein. Desirably, the device comprises a sufficient number of reservoirs having a fill ratio of drug formulation volume to device volume of greater than about 50% (e.g., greater than about 55%, greater than about 60%, greater than about 75%, or greater than about 85%). In particular embodiments, the device comprises at least two reservoirs. In other particular embodiments, the device comprises from two to fifty reservoirs. In still other embodiments the device comprises from three to twenty dose reservoirs, from three to ten reservoirs, or from five to ten dose reservoirs (e.g., seven reservoirs). More or fewer reservoirs are also envisioned. The reservoirs within a single device may be the same size. Alternatively, some reservoirs may be larger than others. For example, the first dose may be larger, functioning as a bolus to drive the drug concentration to a therapeutically effective level, and subsequent doses are smaller and serve as maintenance doses. Alternatively, the first dose or first few doses may be smaller than subsequent doses, for example, for the purpose of "weaning" the patient to the drug.

Housing Units

In embodiments, the two or more housing units form a sidewall of the drug delivery device. The sidewall may be formed using a material that is relatively non-permeable to the bodily fluids over the duration of drug release. As used herein, the term "non-permeable" refers to a material that substantially prevents the movement of fluids and molecules through the material for the duration of drug delivery. For example, in particular embodiments the sidewalls are formed of a material that is substantially non-permeable for at least one week, for at least two weeks, or longer, when deployed in vivo. In some embodiments, the sidewall also aids in protecting the drug from exposure to moisture and/or oxygen during shipping and storage of the device before use.

In particular embodiments, the housing units are formed of a biocompatible polymer. In a preferred embodiment, the housing units are formed of a bioerodible polymer. As used herein, the term "bioerodible" refers to a material that eventually is absorbed by the body, for example by the conversion of a material that initially is insoluble in aqueous systems into a material that is soluble in aqueous systems or by hydrolysis or enzymatic cleavage of the polymer. The term "bioerodible" includes materials that degrade in vivo by "surface erosion," "biodegradation" and/or "bioresorption" as understood in the art. Non-limiting examples of bioerodible polymers include poly(lactic acid), poly(glycolic acid), or poly(lactic-co-glycolic acid)s, and poly(anhydride-co-imides). In another embodiment, the housing units may be constructed of a non-bioerodible material, such as polycarbonate, liquid crystal polymer, polyimide, polyurethane, or a combination thereof.

Dose Units/Solid Units and Drug Formulations

The two or more dose units/solid units comprise at least one drug and/or drug formulation. A drug formulation is a composition that comprises a drug. As used herein, the term "drug" includes any therapeutic or prophylactic agent (e.g., an active pharmaceutical ingredient or API). The drug formulation may include one or more pharmaceutically acceptable excipients, which are known in the art.

Depending on the particular device embodiment, the drug formulation may be in essentially any form, such as a pure solid, a semi-solid, a pure liquid, a gel or hydrogel, a solution, an emulsion, a slurry, or a suspension. In a preferred embodiment, the drug formulation is in a monolithic, dry solid form, or in the form of a collection of particles (e.g., microparticles or nanoparticles), particularly for purposes of maintaining or extending the stability of the drug over a commercially and medically useful time, e.g., during storage in a drug delivery device until the drug needs to be administered. These solid forms may be provided by lyophilization of a drug solution or suspension directly in the reservoirs. Alternatively, prefabricated pellets or microtablets that are approximately the size of individual reservoirs may be formed outside the device (e.g., in a mold) and subsequently loaded into the device, for example, in an inert gas environment. The particular formulation in the reservoirs of a single device may be the same as or different from one another across a plurality of the reservoirs.

The drug formulation may include a drug in combination with other materials to control or enhance the rate and/or time of release from the device. In various embodiments, the drug formulation further includes one or more matrix materials. In one example, the matrix material comprises one or more synthetic polymers. Exemplary materials include synthetic polymers, such as PLGA, PEG, PLLA, and/or naturally occurring polymers such as hyaluronic acid, chitosan, and alginate. The natural-occurring polymers may or may not be crosslinked by methods known to the art. In another example, the one or more matrix materials comprise a biodegradable, bioerodible, water-soluble, or water-swellable matrix material. In one embodiment, the therapeutic or prophylactic agent is distributed in the matrix material and the matrix material degrades or dissolves in vivo to controllably release the therapeutic or prophylactic agent. The therapeutic or prophylactic agent may be heterogeneously distributed in the dose unit/solid unit or may be homogeneously distributed in the dose unit/solid unit. The degradation, dissolution, or diffusion properties of the matrix material can provide a means for controlling the release rate of the drug molecules.

The drug may comprise small molecules, large (i.e., macro-) molecules, or a combination thereof. In one embodiment, the large molecule drug is a protein or a peptide.

Representative examples of suitable drugs include vaccines, vectors for gene therapy, polypeptides, nucleic acids (DNA, siRNA), interferons, antibodies, anti-inflammatories, hormones, and chemotherapeutic agents. In various other embodiments, the drug can be selected from amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants (e.g., LMWH, pentasaccharides), antibiotics (e.g., immunosuppressants), analgesic agents, and vitamins. Examples of suitable types of proteins include, glycoproteins, enzymes (e.g., proteolytic enzymes), hormones or other analogs (e.g., LHRH, steroids, corticosteroids, growth factors), antibodies (e.g., anti-VEGF antibodies, tumor necrosis factor inhibitors), cytokines (e.g., $\alpha$-, $\beta$-, or $\gamma$-interferons), interleukins (e.g., IL-2, IL-10), and diabetes/obesity-related therapeutics (e.g., insulin, exenatide, PYY, GLP-1 and its analogs, rimonabant). In one embodiment, the drug is a gonadotropin-releasing (LHRH) hormone analog, such as leuprolide. In another exemplary embodiment, the drug comprises parathyroid hormone, such as a human parathyroid hormone or its analogs, e.g., hPTH(1-84) or hPTH(1-34). In a further embodiment, the drug is selected from nucleosides, nucleotides, and analogs and conjugates thereof. In yet another embodiment, the drug comprises a peptide with natriuretic activity, such as atrial natriuretic peptide (ANP), B-type (or brain) natriuretic peptide (BNP), C-type natriuretic peptide (CNP), or dendroaspis natriuretic peptide (DNP). In still another embodiment, the drug is selected from diuretics, vasodilators, inotropic agents, anti-arrhythmic agents, $Ca^+$ channel blocking agents, anti-adrenergics/sympatholytics, and renin angiotensin system antagonists. In one embodiment, the drug is a VEGF inhibitor. VEGF antibody, VEGF antibody fragment, or another anti-angiogenic agent. Examples include an aptamer, such as MACUGEN™ (Pfizer/Eyetech) (pegaptanib sodium)) or LUCENTIS™ (Genetech/Novartis) (rhuFab VEGF, or ranibizumab), which could be used in the prevention of choroidal neovascularization (useful in the treatment of age-related macular degeneration or diabetic retinopathy). In yet a further embodiment, the drug is a prostaglandin, a prostacyclin, or another drug effective in the treatment of peripheral vascular disease. In still another embodiment, the drug is an angiogenic agent, such as VEGF. In a further embodiment, the drug is an anti-inflammatory such as dexamethasone. In one embodiment, a device includes both angiogenic agents and anti-inflammatory agents. A single device may include a single drug or a combination of two or more drugs.

The release of drug from the device may be tailored to provide a temporally modulated release profile (e.g., pulsatile release) when time variation in plasma levels is desired or a more continuous or consistent release profile when a constant plasma level as needed to enhance a therapeutic effect, for example. Pulsatile release, or intermittent release, can be achieved from an individual dose unit, from a plurality of dose units, or a combination thereof. For example, where each dose unit provides only a single pulse, multiple pulses (i.e. pulsatile release) are achieved by temporally staggering the single pulse release from each of several dose units. Alternatively, multiple pulses can be achieved from a single dose unit by incorporating several layers of a release system and other materials into a single dose unit. Continuous release can be achieved by incorporating a release system that degrades, dissolves, or allows diffusion of molecules through it over an extended period. In addition, continuous release can be approximated by releasing several pulses of molecules in rapid succession.

In one embodiment, the drug formulation within a dose unit comprises layers of a drug or drugs and a non-drug material, wherein the multiple layers provide pulsed drug release due to the intervening layers of non-drug. Such a strategy can be used to obtain complex release profiles.

Discrete Timing and Seal Members

Dose units may be separated from each other by at least one timing member or seal member, membrane, film, or other structure. For example, a discrete timing member or seal member may be disposed between each dose unit. The discrete timing member or seal member functions to protect the dose unit (e.g., the drug formulation) until such time as release of the dose unit is desired. A discrete timing member or seal member may be a thin film or other structure suitable for separating a dose unit from the environment outside of the device. The discrete timing members or seal members are formed from a material or mixture of materials that are degradable. As used herein, the term "degradable" refers to a material that will biodegrade, bioerode, dissolve, or otherwise rupture in contact with fluids and tissues in vivo.

Each of the discrete timing members or seal members are designed to open at specified times, thereby delivering the dose unit sequentially at pre-specified times. These discrete timing members or seal members may be independently degraded or groups of the discrete timing members or seal members may degrade substantially simultaneously. For example, in certain embodiments the discrete timing members or seal members disposed at distal ends of the device are exposed to the environment outside of the device and degrade substantially simultaneously, such that dose units are released substantially simultaneously from distal ends of the device. Desirably, the exposure of the dose unit to the environment is passively controlled through the rupture of the discrete timing member or seal member. In a passive control system for example, the timing can be controlled by selecting the discrete timing member or seal member dimension, composition, and structure.

The compositions of the discrete timing member or seal member may be selected from materials that will rupture in response to an environment existing in vivo in the patient or in response to a component contained in the reservoir. Examples of environmental conditions include, but are not limited to temperature, water, pH, an electrolyte, and enzymes.

In preferred embodiments, the discrete timing members or seal members are selected to degrade in vivo, without any intervention by the patient or caregiver (subsequent to deployment). In one particular embodiment, the discrete timing members or seal members are formed of a biocompatible polymer, such as a poly(lactic acid), poly(glycolic acid), or poly(lactic-co-glycolic acid)s, as well as degradable poly(anhydride-co-imides), of a composition and thickness designed to disintegrate by hydrolysis in a prescribed timeframe, releasing the drug contained in the dose unit. For example, the discrete timing member or seal member may have a thickness ranging from about 0.1 mm to about 1.0 mm, e.g., 0.2 mm to 0.8 mm.

In a preferred embodiment, a discrete timing member or seal member completely separates the dose units from each other. In another embodiment, discrete timing members or seal members separate only a portion of the dose units from each other.

Representative examples of discrete timing members or seal members include degradable polymeric and non-polymeric materials. In a preferred embodiment, the discrete timing members or seal members are formed of a bioerodible or biodegradable material known in the art, such as a synthetic polymer or copolymer, e.g., a polyester (such as PLGA), a poly(anhydride), or a polycaprolactone. The discrete timing members or seal members may be a multilayer structure. For example an inner layer may be porous or otherwise control diffusion once the outer, non-permeable layer has disintegrated. The discrete timing members or seal members of a single device may be made of different materials, may have different thicknesses, may have different degrees of cross-linking, or a combination thereof, for the purpose of opening different dose units at different times relative to one another. Regardless of their construction, the timing members generally are designed to degrade before the housing units can degrade, or at least before the housing units degrade sufficiently to lose structural integrity that would adversely affect the sequentially controlled release of the doses of drug.

Exemplary Embodiments

The foregoing embodiments of devices and methods for their use can be further understood with reference to the appended drawings and description below, where like numbers refer to the same device or component.

Figure 1A:
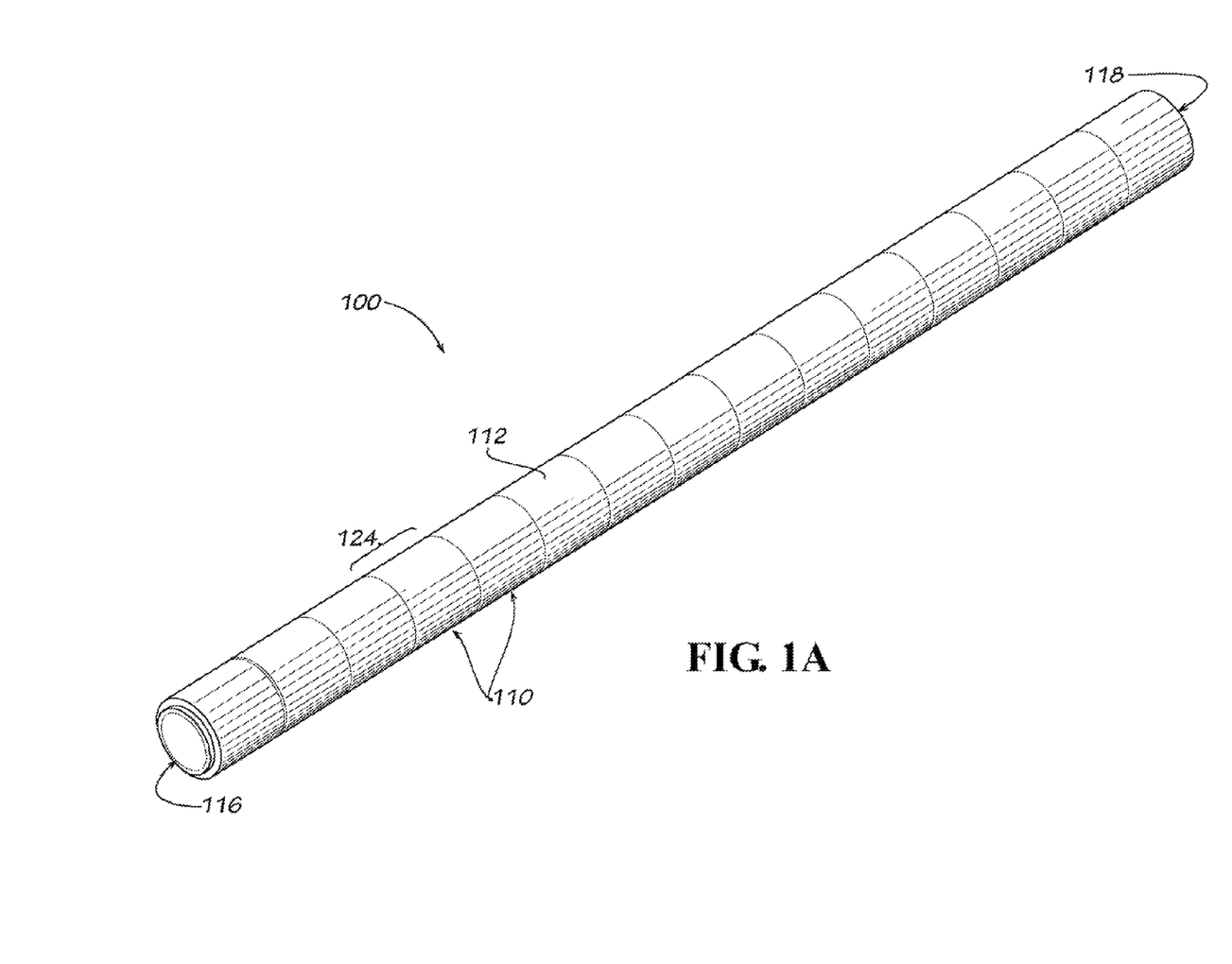
FIG. 1A is a perspective view of an embodiment of an implantable drug delivery device.
Figure 1B:
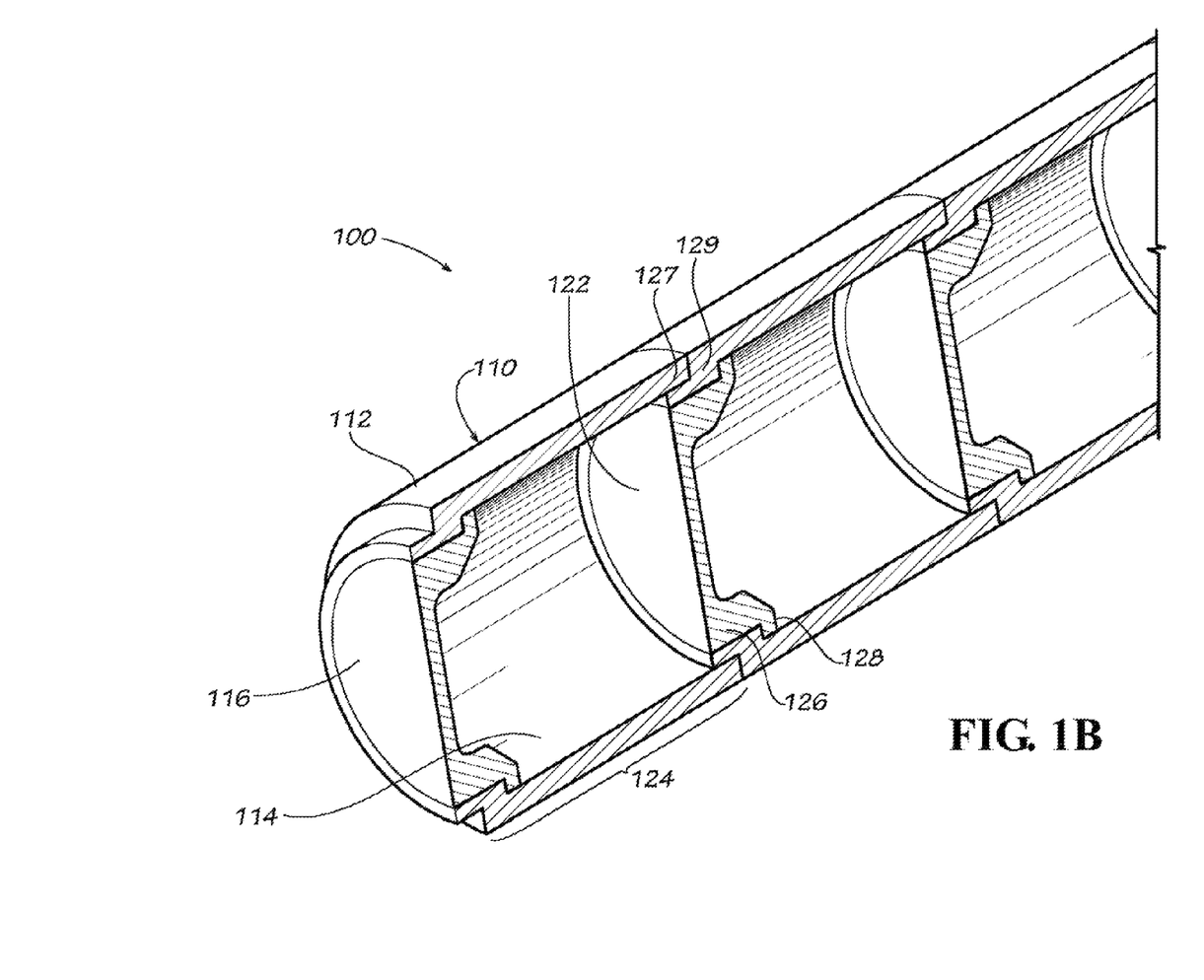
FIGS. 1B and 1C are partial cross-sectional views of the implantable drug delivery device of FIG. 1A without and with, respectively, discrete dose units disposed therein.
Figure 1C:
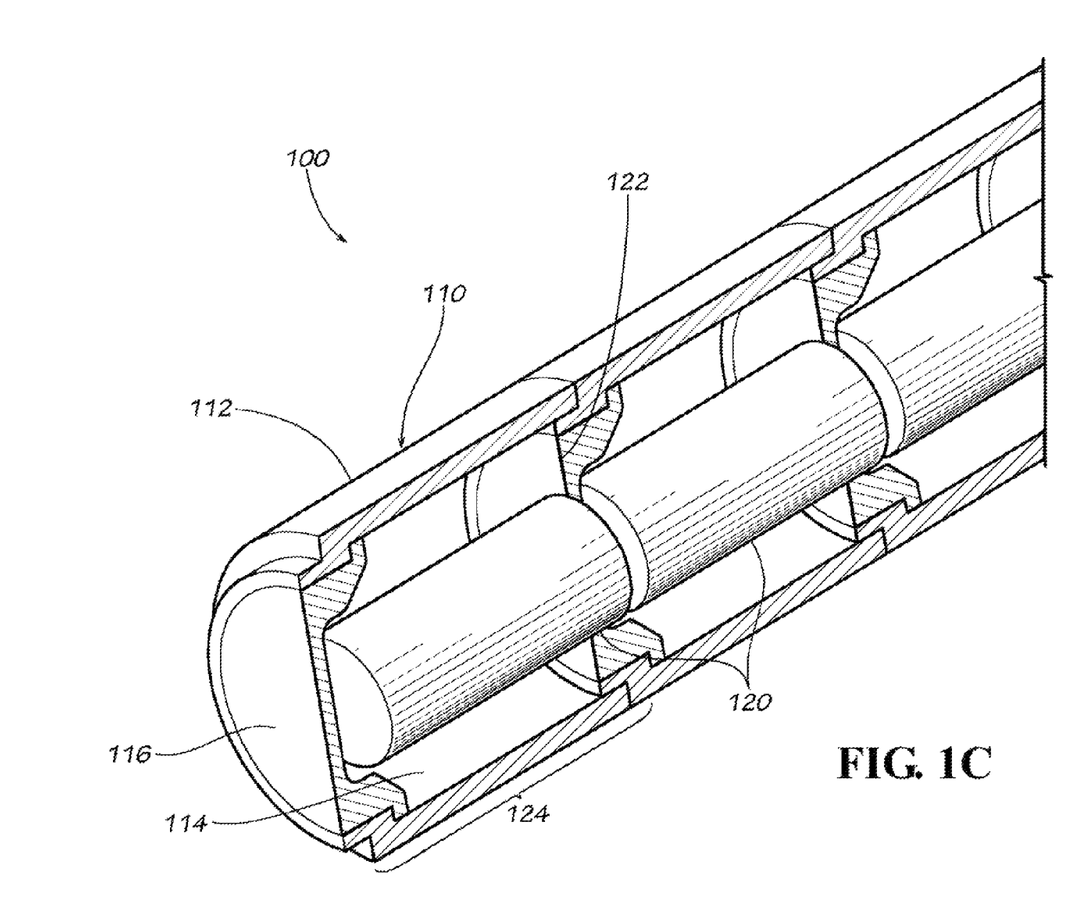

An embodiment of a drug delivery device 100 illustrated in FIGS. 1A-1C has a plurality of housing units 110, each housing unit 110 having an exterior surface 112 and an interior surface 114. Fifteen housing units are shown in FIG. 1A, although other numbers are readily envisioned. The exterior surfaces 112 of the connected housing units 110 define a sidewall. The housing units 110 are located between a first end piece 116 defining a first end of the device and a second end piece 118 defining a second end of the device distal to the first end of the device. Although not shown, the first and/or second end piece may have a tapered or point end to facilitate tissue penetration during the insertion/deployment process.

A plurality of discrete dose units 120, each comprising at least one drug, are disposed within the housing units 110 located between the first 116 and second end pieces 118. The dose unit may be a drug formulation which includes the at least one drug. The device 110 further includes degradable timing members 122 connected to the housing units 124 and separating the discrete dose units 120 from one another. The timing member 122, the first end piece 116 (or a second timing member 122 or second end piece 118), and the interior surface of the housing unit 114 to which the first end piece (or a second timing member 122 or second end piece 118) is connected together define a reservoir 124 in which one of the dose units 120 is disposed. It should be appreciated that for illustration purposes the dose units shown in FIGS. 1C and 1D do not completely fill the reservoir 124. Each reservoir in preferred embodiments would be completely or at least substantially filled with the dose units so as to maximize the amount of drug loaded in the device.

Figure 1D:
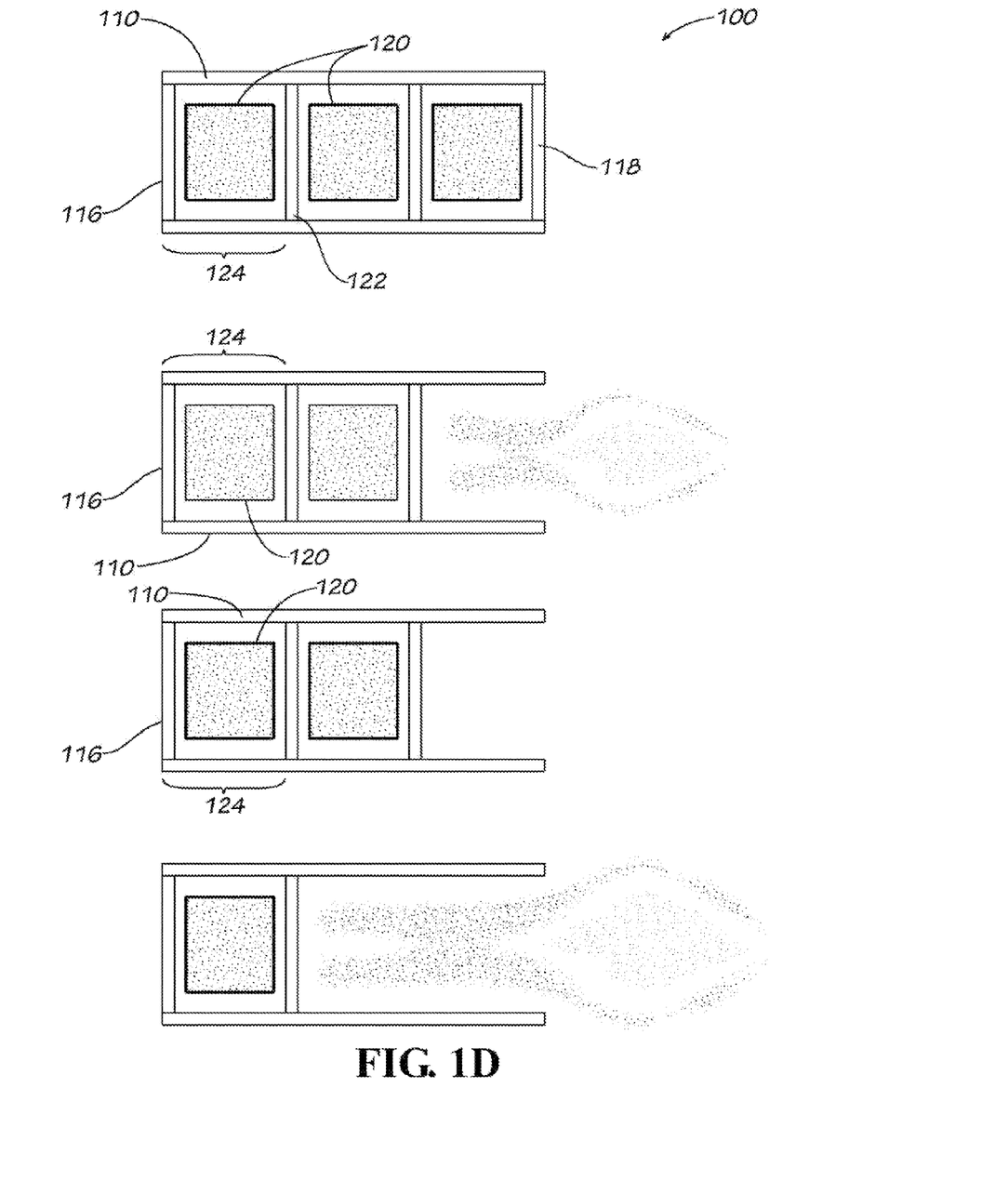
FIG. 1D is a schematic illustration of the timed sequential release of drug from the drug implantable drug delivery device of FIGS. 1A-1C.
Figure 2:
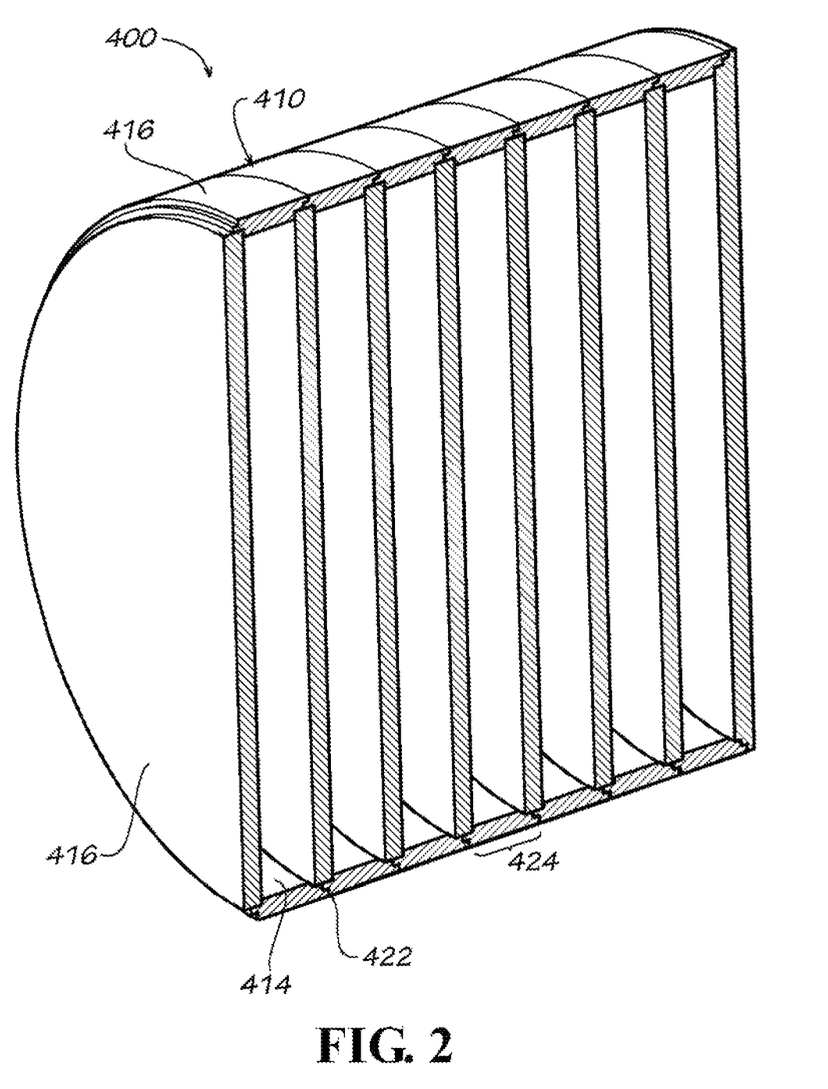
FIG. 2 is a cross-sectional view of an embodiment of an implantable drug delivery device.

The device is adapted to release a first discrete dose unit 120 following rupture of the first 116 or second end piece 118, and subsequently to release a second discrete dose unit 120 following rupture of a degradable timing member 122. The device subsequently releases one or more additional discrete dose units 120 following rupture of one or more additional degradable timing members 122. A schematic illustration of the timed release from a drug delivery device according to the foregoing embodiment is illustrated in FIG. 1D.

Figure 5:
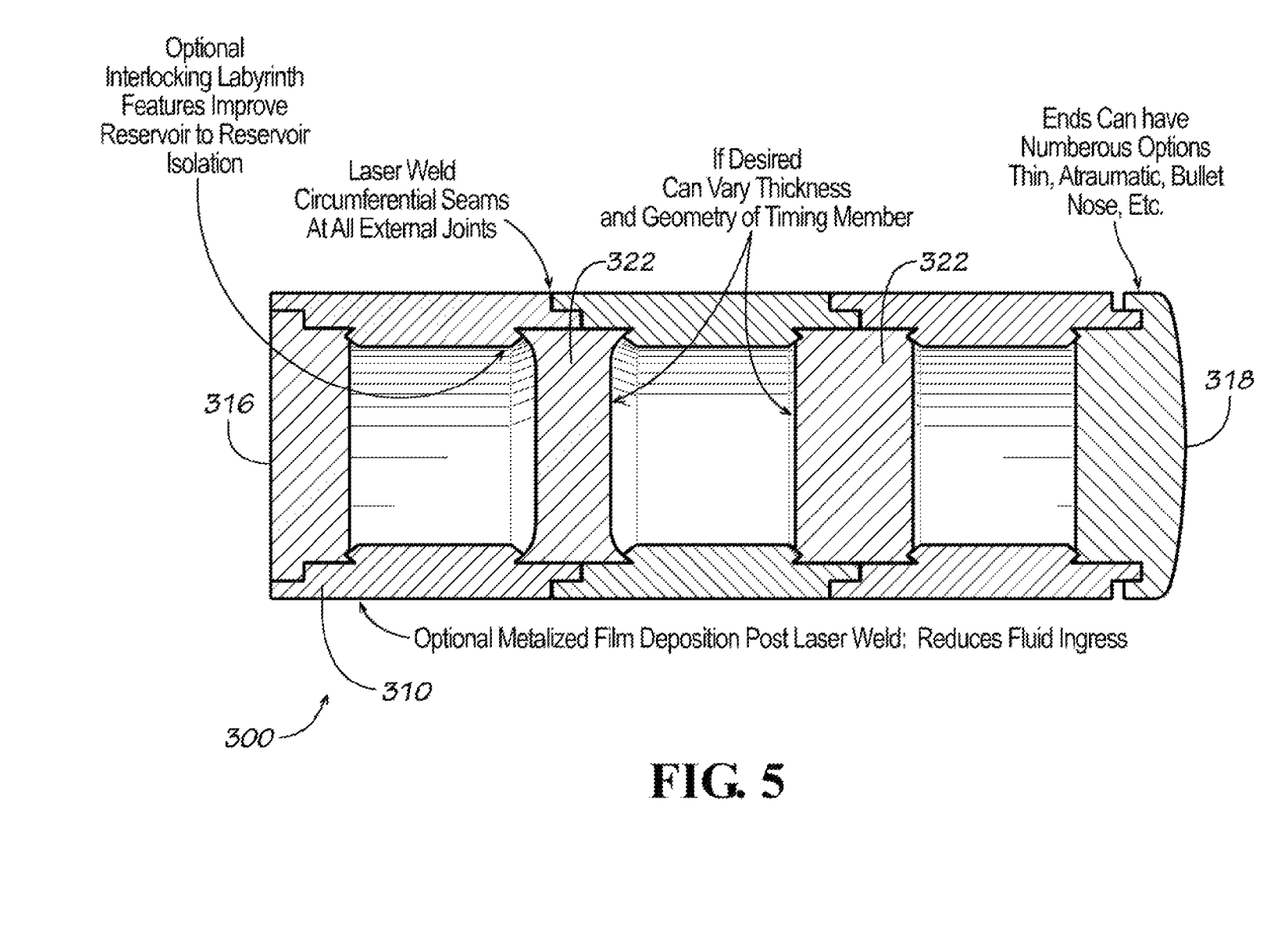
FIG. 5 is a cross-sectional view of an embodiment of an implantable drug delivery device.

In one embodiment of the drug delivery device 110, one of the housing units 110 has a flange 126 defining a shoulder 129. An end 127 of the other of the housing units is mated with the flange 126 and the shoulder 129 of the adjacent housing unit or end piece. The at least one timing member 122 may comprise a flange 128 that is mated with the flange 126 of the housing unit 110 and with the interior surface 114 of the housing unit. The drug delivery device 100 optionally further comprises a coating (e.g., a metalized film deposition or polymer) on the exterior surfaces 112 of the housing units 110 as shown in FIG. 5.

Those skilled in the art will appreciate that the geometry and dimensions of the drug delivery device and its components (i.e., housing unit, dose unit, degradable timing member, etc.) may be modified from the present description to satisfy various design needs. Exemplary dimensions of devices are discussed below for FIGS. 3-4, with FIGS. 3A and 4A illustrating the housing units and FIGS. 3B and 4B illustrating degradable timing members of embodiments of the drug delivery device.

Figure 3A:
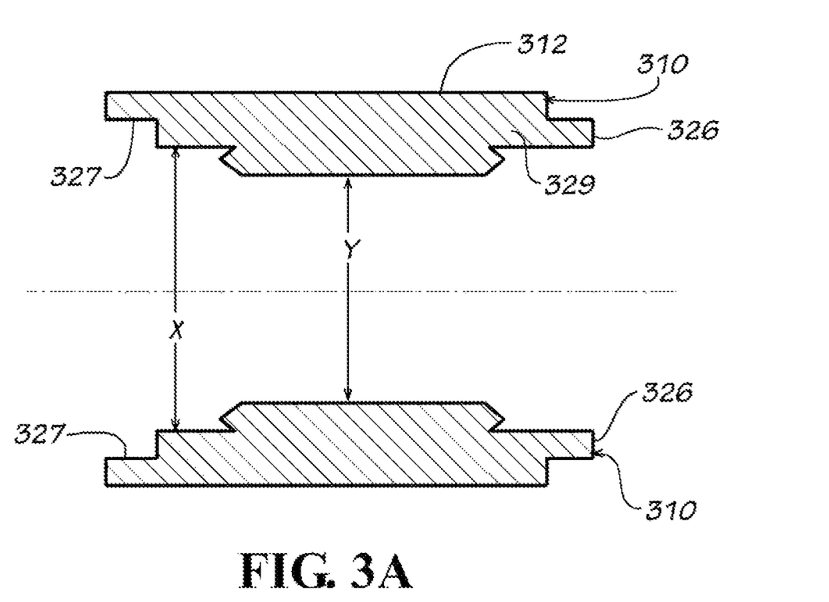
FIGS. 3A and 3B are schematic illustrations of a single housing unit and a single degradable timing member, respectively, of the implantable drug delivery device of FIG. 5.

For example, in an exemplary embodiment the housing unit 310 illustrated in FIG. 3A has a length in the longitudinal direction of approximately 0.040 inches, an exterior surface 312 diameter of approximately 0.040 inches, an interior surface 314 diameter (X) of approximately 0.030 inches, a flange 326 having a length of approximately 0.003 inches, a shoulder 329 having a length of approximately 0.004 inches, and an end 327 having a length of approximately 0.003 inches for mating with the flange 326 and shoulder 329 of the adjacent housing unit. In an embodiment, the relative interior surface and exterior surface diameters of the housing units at the end 327 and flange 326 of the housing units, respectively, are such that the flange 326 of a first housing unit snugly fits within the end 327 of an adjacent second housing unit (illustrated in FIG. 5). For example, in an embodiment the housing unit 310 of FIG. 3A may have an interior surface diameter at the end 327 of 0.0365 inches and an exterior surface 312 diameter at the flange 326 of 0.0370 inches, such that the diameter of the flange-side of the housing unit would be compressed when mated with the adjacent housing unit. Alternatively, the housing unit 310 of FIG. 3A may have an interior surface diameter at the end 327 of 0.037 inches and an exterior surface diameter at the flange 326 of 0.0365 inches, such that the diameter of the flange-side of the housing unit would readily mate with the end-side of the adjacent housing unit without being compressed. In embodiments, the degradable timing member 322 illustrated in FIG. 3B has an outer diameter of approximately 0.0335 inches and a width in the longitudinal direction of approximately 0.010 inches. The degradable timing member illustrated in FIG. 3B is disposed within the overlapping flange 326 and shoulder 329 of adjacent housing units 310 illustrated in FIG. 3A and may have a feature that interlocks with a portion of the housing units 310 to improve the isolation of the adjacent reservoirs (FIG. 5). In certain embodiments, other means may be used to secure adjacent housing units. For example, laser welds may be used to join circumferential seams of the housing units, a metalized film or other coating may be applied to the exterior surface of the assembled housing units, or adhesives may be used to secure adjacent housing units and degradable timing members.

Figure 3B:
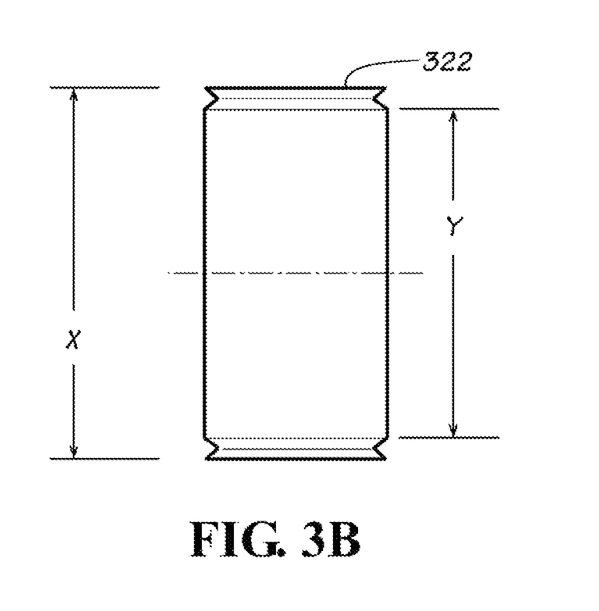
Figure 4A:
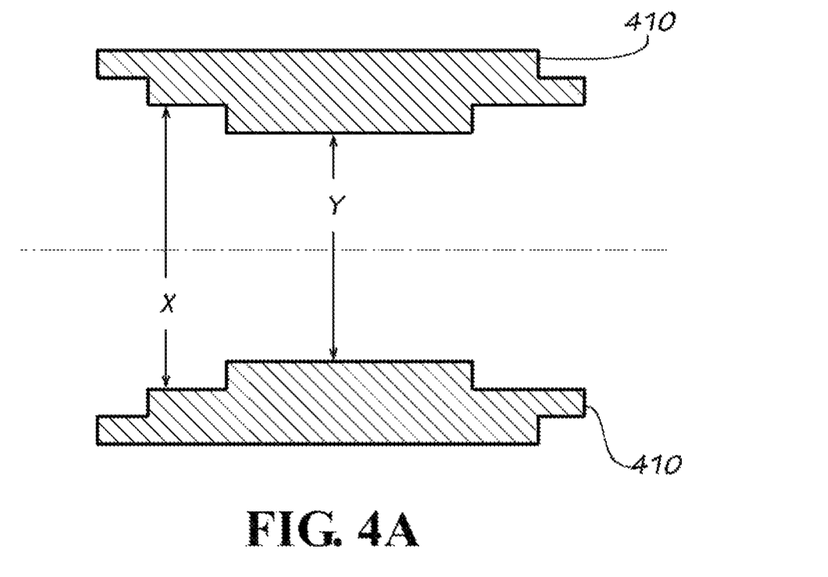
FIGS. 4A and 4B are schematic illustrations of a single housing unit and a single degradable timing member, respectively, of the implantable drug delivery device of FIG. 2.
Figure 4B:
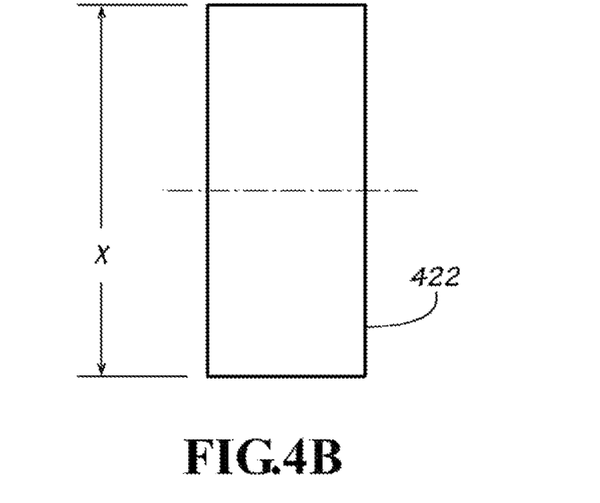

The housing unit 410 and degradable timing member 422 illustrated in FIGS. 4A and 4B, respectively, are similar to those illustrated in FIGS. 3A and 3B; however, they exclude the interlocking feature of the housing units and degradable timing members.

Figure 6A:
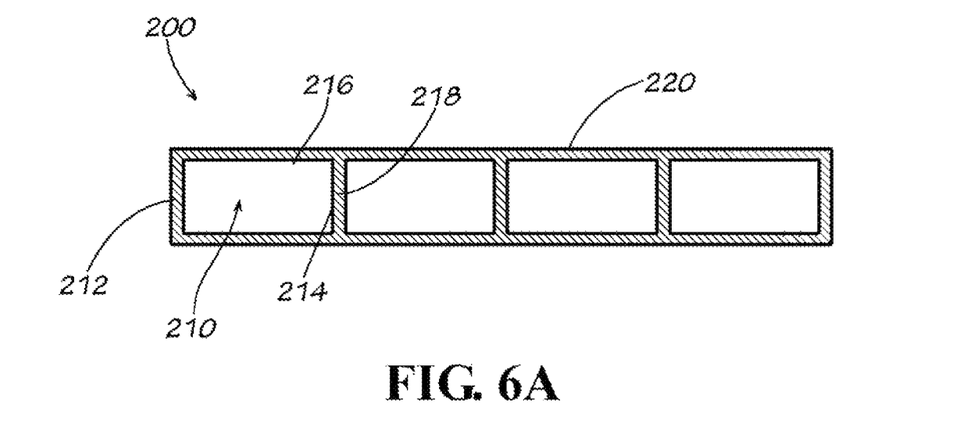
FIGS. 6A and 6B are a cross-sectional illustration and exploded perspective illustration, respectively, of an embodiment of an implantable drug delivery device.
Figure 6B:
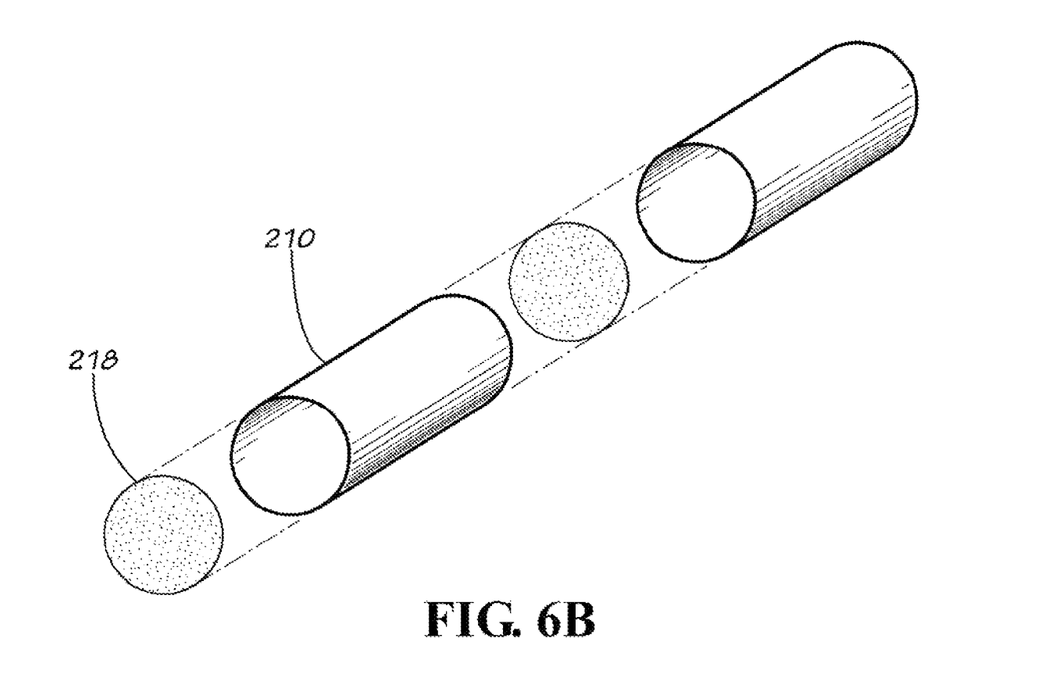

Another exemplary embodiment of a drug delivery device is illustrated in FIG. 6. The device 200 comprises a plurality of solid units 210 of a drug formulation which comprises at least one drug. The solid units 210 each have a proximal end 212, a distal end 214, and one or more longitudinal exterior surfaces 216 therebetween. At least one seal member 218 is sandwiched between the proximal end 212 of a first solid unit 210 and the distal end 214 of a second solid unit 210. A coating layer 220 covers at least the longitudinal exterior surfaces 216 of the solid units 210. Desirably, the coating layer 220 is substantially non-permeable such that release of the drug from the solid units 210 is controlled at least in part by the in vivo disintegration of the seal member 218. In particular embodiments, the solid units 210 each have a cylindrically shaped exterior surface 216 and the seal member 218 is disk shaped.

Making the Devices

The basic methods of fabricating and assembling the drug delivery devices described herein are known or can be readily adapted from techniques known in the art. In one embodiment, the housing units, timing membranes, and seal members are made by casting or molding, such as by injection molding. Micromachining and drilling processes may also be used in the product of the components. The components can be assembled and secured together using a variety of techniques including, but not limited to, the use of adhesives, heat or solvent welding, and/or mechanical fasteners. In one embodiment, two or more components may joined together using laser welding.

Implanting/Using the Devices

The devices described herein can be used in a variety of therapeutic, prophylactic, or diagnostic medical applications. In a preferred embodiment, the devices store and release an effective amount of at least one drug formulation over an extended period, e.g., between 1 week and 12 months.

The device may be implanted into a patient (such as a human or other vertebrate animal) using standard surgical or more preferably a minimally invasive implantation technique, (e.g., by a small incision or injection through a needle, trocar, cannula, catheter, or the like) or noninvasive implantation technique (e.g., swallowing). Ultrasound, nuclear magnetic resonance, virtual anatomic positioning systems, or other imaging techniques may be employed to confirm proper positioning of the implant. In various embodiments, the administration system may include a catheter, wire, tube, endoscope, or other mechanism capable of reaching the desired recipient anatomic site through an incision, puncture, trocar, or through an anatomic passageway such as a vessel, orifice, or organ lumen, or trans-abdominally or trans-thoracically. In various embodiments according to the present invention, the delivery system may be steerable by the operator.

In one embodiment, the device may be dimensioned for delivery from a 6 to 26 gauge (approximately 0.439 inches to 0.241 inches nominal ID) needle. Larger or smaller gauges of modified needles may also be used to accommodate various sized drug delivery devices described herein. It may be preferable to implant devices that have larger diameters using means known in the art other than needles. In certain embodiments the drug delivery device may be inserted through a small incision, wherein the incision length is approximately equal to the diameter of the device. In certain embodiments, the drug delivery device described herein may be delivered using apparatus and techniques described, for example, in U.S. Pat. No. 7,214,206 and U.S. Pat. No. 7,104,945, which are incorporated herein by reference.

Drug may then be passively released locally at the tissue site of implantation using a preselected delivery profile (e.g., dosing schedule) based on the design of the particular device as prescribed by the patient's physician. For example, in embodiments the drug is released in a controlled and sustained manner to provide a desired local or systemic physiological or pharmacological effect over a desired time period (e.g., one weeks to 12 months). Alternatively, in certain embodiments the drug is released in a pulsatile manner to provide the desired local or systemic physiological or pharmacological effect over the desired time period.

Modifications and variations of the methods and devices described herein will be obvious to those skilled in the art from the foregoing detailed description. Such modifications and variations are intended to come within the scope of the appended claims.

I claim:

1. A drug delivery device comprising:
   at least two housing units connected together end-to-end in a fixed, linear orientation, each housing unit having an exterior surface and an interior surface, the exterior surfaces of the connected housing units defining a sidewall of the device;
   at least two discrete dose units, each comprising a drug formulation comprising at least one drug, wherein each of the housing units has one of the discrete dose units disposed therewithin;
   at least one degradable timing member connected to the at least two housing units and separating the discrete dose units from one another;
   a first end piece defining a first end of the device; and second end piece defining a second end of the device distal to the first end of the device, the discrete dose units being located between the first and second end pieces within each of the housing units, wherein the device, when deployed in vivo, is adapted to release a first of the at least two discrete dose units following rupture of the first or second end piece, and subsequently to release a second of the at least two discrete dose units following rupture of the at least one degradable timing member separating the first of the at least two discrete dose units from the second of the at least two discrete dose units.

2. The device of claim 1, wherein the device is substantially tubular in shape.

3. The device of claim 1, wherein the elongated body is formed of a polymer.

4. The device of claim 1, wherein at least one of the housing units is formed of a bioerodible polymer.

5. The device of claim 1, wherein the device comprises from three to fifty housing units, each housing unit having a discrete dose unit disposed therewithin.

6. The device of claim 1, wherein the device is dimensioned for insertion into a patient via a needle, trocar, catheter, or incision.

7. The device of claim 1, wherein the drug formulation is in a solid, semi-solid, or gel drug form.

8. The device of claim 1, wherein the timing member, the first end piece, and the interior surface of the housing unit to which the first end piece is connected, together define a reservoir in which one of the discrete dose units is disposed.

9. The device of claim 1, wherein one of the at least two housing units has a flange defining a shoulder, an end of the other of the at least two housing units being mated with the flange and the shoulder.

10. The device of claim 9, wherein the at least one timing member comprises a flange that is mated with the flange of the housing unit and with the interior surface of the housing unit.

11. The device of claim 1, wherein the device has a fill ratio of drug formulation volume to device volume of greater than 50%.

12. An implantable drug delivery device comprising:
at least two solid units of a drug formulation which comprises at least one drug, the solid units each having a proximal end, a distal end, and one or more longitudinal exterior surfaces therebetween;
at least one seal member sandwiched between the proximal end of a first of the at least two solid units and the distal end of a second of the at least two solid units; and
a coating layer covering at least the longitudinal exterior surfaces of the solid units, the coating layer being substantially non-permeable,
wherein release of the drug from the first or second solid unit is controlled at least in part by the in vivo disintegration of the seal member.

13. The drug delivery device of claim 12, wherein the solid units each have a cylindrically shaped exterior surface and the seal member is disk shaped.

14. The drug delivery device of claim 12, wherein the seal member comprises a bioerodible polymer.

15. The drug delivery device of claim 12, wherein the coating layer comprises a bioerodible polymer that disintegrates in vivo after the in vivo disintegration of the seal member and the release of the drug from the device.

16. The device of claim 12, wherein the device comprises from three to fifty solid units.

17. The device of claim 12, wherein the device is dimensioned for insertion into a patient via a needle, trocar, catheter, or incision.

* * * * *

UNITED STATES PATENT AND TRADEMARK OFFICE
CERTIFICATE OF CORRECTION

PATENT NO.         : 8,679,093 B2                                    Page 1 of 1
APPLICATION NO.    : 13/302863
DATED              : March 25, 2014
INVENTOR(S)        : Robert Farra It is certified that error appears in the above-identified patent and that said Letters Patent is hereby corrected as shown below:

In the Claims:

At column 11, line 1, before the "second end piece" insert --a--.

Signed and Sealed this
Tenth Day of June, 2014

Michelle K. Lee
*Deputy Director of the United States Patent and Trademark Office*